United States Patent
Wada

(10) Patent No.: US 9,678,081 B2
(45) Date of Patent: Jun. 13, 2017

(54) CHROMATOGRAPHY METHOD AND CHROMATOGRAPHIC KIT

(71) Applicant: FUJIFILM Corporation, Tokyo (JP)

(72) Inventor: Atsuhiko Wada, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 50 days.

(21) Appl. No.: 14/037,853

(22) Filed: Sep. 26, 2013

(65) Prior Publication Data

US 2014/0087367 A1   Mar. 27, 2014

(30) Foreign Application Priority Data

Sep. 27, 2012   (JP) ................................. 2012-213916

(51) Int. Cl.
*G01N 33/58*   (2006.01)
*G01N 33/558*   (2006.01)

(52) U.S. Cl.
CPC ......... *G01N 33/585* (2013.01); *G01N 33/558* (2013.01)

(58) Field of Classification Search
None
See application file for complete search history.

(56) References Cited

U.S. PATENT DOCUMENTS

| 6,146,589 | A | 11/2000 | Chandler | |
|---|---|---|---|---|
| 2008/0166745 | A1* | 7/2008 | Khan et al. | 435/11 |
| 2009/0203147 | A1* | 8/2009 | Katada | 436/80 |
| 2010/0233708 | A1* | 9/2010 | Mehra et al. | 435/6 |
| 2011/0136258 | A1* | 6/2011 | Sambursky et al. | 436/501 |
| 2012/0058465 | A1 | 3/2012 | Mori et al. | |
| 2012/0070822 | A1* | 3/2012 | Bae et al. | 435/5 |

FOREIGN PATENT DOCUMENTS

| JP | 2002-202307 A | 7/2002 |
|---|---|---|
| JP | 2009-192226 A | 8/2009 |
| JP | 2009-216695 A | 9/2009 |
| JP | 2009-216696 A | 9/2009 |
| JP | 2010-230634 A | 10/2010 |
| WO | WO 2013/042815 A1 | 3/2013 |

OTHER PUBLICATIONS

Japanese Office Action and English translation thereof, dated Aug. 26, 2014, for Japanese Patent Application No. 2012-213916.
Extended European Search Report issued in European Patent Application No. 13186119.7 on Nov. 14, 2013.
Cho et al., "Immunogold-silver staining-on-a-chip biosensor based on cross-flow chromatography", Journal of Chromatography B, vol. 878, pp. 271-277, 2010.

\* cited by examiner

*Primary Examiner* — Rebecca Martinez
(74) *Attorney, Agent, or Firm* — Birch, Stewart, Kolasch & Birch, LLP

(57) ABSTRACT

The chromatography method includes a step of forming a composite with a test substance and a labeling substance containing a metal modified by a first binding substance of the test substance and then developing the composite on an insoluble carrier; a step of capturing the test substance and the labeling substance in a detection site on the insoluble carrier including a second binding substance of the test substance or a substance having a binding property to the first binding substance of the test substance; and a step of amplifying the captured labeling substance using a first amplification reagent and a second amplification reagent to detect the test substance.

8 Claims, 3 Drawing Sheets

CHROMATOGRAPHY METHOD AND CHROMATOGRAPHIC KIT

BACKGROUND OF THE INVENTION

1. Field of the Invention

The present invention relates to a chromatography method and a chromatographic kit, in which a signal amplification operation is carried out in order to increase detection sensitivity.

2. Description of the Related Art

Among immunoassay methods, an immunochromatography method is generally used in many cases since it is easily handled and allows measurement to be performed in a short time. As an immune reaction used in an immunochromatography method, a competitive type reaction or a sandwich reaction is widely used. Between these, the sandwich reaction is mainly used in an immunochromatography method, and as a typical example thereof, the following operation is carried out to detect a test substance formed of an antigen in a sample. First, fine particles sensitized with antibodies to antigens which are test substances are immobilized to chromatographic carriers as fine solid phase particles, or the antibodies themselves are directly immobilized to the chromatographic carriers, whereby chromatographic carriers having reaction sites are prepared. Meanwhile, fine labeling particles are sensitized with antibodies which can bind specifically to the test substances, whereby sensitized fine labeling particles are prepared. These sensitized fine labeling particles and a sample move together on the chromatographic carriers in a chromatographic manner. By these operations, immobilized antibodies become an immobilization reagent in the reaction sites formed in the chromatographic carrier, and the sensitized fine labeling particles bind specifically to the antibodies via antigens which are test substances. Consequently, the presence or absence or the degree of the signals which are generated when the sensitized fine labeling particles are captured by the reaction sites is visually determined, whereby the presence or absence or the amount of the test substances included in the sample can be measured.

In the immunochromatography method, in order to avoid a problem (risk) that the antigen is not detected due to the low sensitivity, a method of amplifying detection signals is carried out in some cases. As the signal amplification method, an enzyme such as alkaline phosphatase and peroxidase is used as a label in some cases, or, detection is carried out by increasing the sensitivity by using a compound containing silver and a reductant for silver ions for a label selected from a group consisting of a metallic colloid label and a metallic sulfide label (silver amplification) in some cases. The immunochromatography method using such amplification is described in JP2002-202307A, JP2009-216695A, and JP2009-216696A, Journal of Chromatography, 878 (2010) 271-277, and the like.

SUMMARY OF THE INVENTION

In the immunochromatography method for detection signal amplification, two solutions, a solution for catalyzing amplification and a solution for carrying out amplification are used, but unless the site for adding the solutions, in particular, the first solution, or the flowing direction or timing is not defined, the amplification reaction is sometimes not carried out normally, and the background signal increases, whereby the test substance cannot be properly detected. Further, in the case where it is desired to check the results as in influenza diagnosis, speedy measurement is important, the test time is preferably as short as possible, and a simple and convenient measurement is also important.

In JP2002-202307A, there is described a method for adding a silver amplification solution to a detection zone dropwise; in this method, amplification failure occurs in some cases. In Journal of Chromatography, 878 (2010) 271-277, normal amplification is successfully conducted by setting the development direction of a sensitivity increasing solution angled at 90 degrees with respect to the development direction of a specimen solution, but there is a problem in terms of simplicity and convenience since replacement of component members is required. Further, in the method of Journal of Chromatography, 878 (2010) 271-277, there is a problem in terms of rapidity since it takes 20 minutes or longer for the operation to be completed. In JP2009-216695A and JP2009-216696A, a method for flowing an amplification solution or a washing solution before amplification, or a one-solution for increasing sensitivity is successful in normal amplification with good sensitivity by applying an angle with respect to the development direction of a specimen solution, but replacement of component members is required and the rapidity and the convenience are not sufficient. In addition, in an immunochromatography method for amplifying a detection signal using an amplification solution, in the case where it is not necessary to set the amplification solution angled with respect to the development direction of a specimen solution, that is, is flowed in the same direction as the development direction of the specimen solution, there is a problem of an increase in the background signals in some cases.

A problem to be solved by the present invention is to provide a chromatography method and a chromatographic kit, with which normal amplification can be carried out, background signals can be inhibited, and the operation is simple and convenient, and thus, measurement can be carried out rapidly.

The present inventors have made an extensive investigation to solve the above-mentioned problems, and as a result, they have found that by adding a first amplification reagent to a position further upstream in the development direction than a position on the insoluble carrier to which a test sample containing a test substance is added, thereby developing the first amplification reagent and the test sample in the same direction; adding a first amplification solution onto the insoluble carrier within 0 seconds to 1 minute and 30 seconds after the test sample is added onto the insoluble carrier; and infiltrating a second amplification reagent into the insoluble carrier in the thickness direction of the insoluble carrier, a normal amplification reaction can be accomplished, background signals can be inhibited, and measurement can be carried out rapidly, thereby completing the present invention.

Specifically, according to the present invention, there is provided a chromatography method including:

a step of forming a composite with a test substance and a labeling substance containing a metal modified by a first binding substance of the test substance and then developing the composite on an insoluble carrier;

a step of capturing the test substance and the labeling substance in a detection site on the insoluble carrier including a second binding substance of the test substance or a substance having a binding property to the first binding substance of the test substance; and a step of amplifying the captured labeling substance using a first amplification reagent and a second amplification reagent to detect the test substance, in which the position on the insoluble carrier to which the first amplification reagent is added is further upstream in the development direction than the position on the insoluble carrier to which the test sample containing the test substance is added;

the first amplification reagent is added onto the insoluble carrier within 0 seconds to 1 minute and 30 seconds after the test sample is added onto the insoluble carrier;

the first amplification reagent and the test sample are developed in the same direction on the insoluble carrier; and the second amplification reagent is infiltrated into the insoluble carrier in the thickness direction of the insoluble carrier.

It is preferable that the first amplification reagent be added onto the insoluble carrier within 0 seconds to 30 seconds after the test sample is added onto the insoluble carrier.

It is preferable that the development direction of the test sample and the first amplification reagent be the longitudinal direction of the insoluble carrier.

It is preferable that the second amplification reagent be supplied to a gap having a height of 0.01 mm to 1 mm provided on the upper surface side of the insoluble carrier, and the second amplification reagent supplied to the gap be infiltrated into the insoluble carrier in the thickness direction of the insoluble carrier.

It is preferable that the first amplification reagent be a reductant for silver ions and the second amplification reagent be a compound containing silver.

It is preferable that the first amplification reagent be a reagent containing divalent iron ions.

It is preferable that the insoluble carrier have an area having a color developing reagent for detecting the first amplification reagent.

It is preferable that the area having a color developing reagent be located further downstream than the detection site on the insoluble carrier.

It is preferable that the color developing reagent be a compound which develops color by reacting with ions.

It is preferable that the color developing reagent be a compound which develops color by reacting with $Fe^{2+}$ ions.

It is preferable that the color developing reagent be a compound having a phenanthroline skeleton.

It is preferable that the color developing reagent be a compound which develops color by reacting with $H^+$ ions.

It is preferable that the first binding substance and/or the second binding substance be an antibody.

It is preferable that the labeling substance be a colloidal metal.

It is preferable that the colloidal metal be a colloidal gold.

According to the present invention, there is provided a chromatographic kit including:

(1) a labeling substance containing a metal modified with a first binding substance of a test substance, (2) a first member having an area to which a test sample containing the test substance is added and a labeling substance capturing area having a second binding substance of the test substance or a binding substance of the first binding substance in this order in the direction from upstream to downstream with respect to the development direction of the test sample containing the test substance; and (3) a second member having a hole positioned to add the first amplification reagent at a position further upstream in the development direction of the test sample than the area to which the test sample containing the test substance is added, and a hole positioned to add the second amplification reagent at a position further downstream in the development direction of the test sample than the labeling substance capturing area.

Preferably, a gap having a height of 0.01 mm to 1 mm is formed on the upper surface of the labeling substance capturing area by arranging the first member and the second member.

Preferably, the first member further has an area having a color developing reagent for detecting the first amplification reagent.

By the chromatographic kit and the chromatography method of the present invention, a normal amplification reaction can be carried out, background signals can be inhibited, and the operation is simple and convenient, and thus, the measurement can be carried out rapidly.

BRIEF DESCRIPTION OF THE DRAWINGS

As shown in FIG. 1, the development direction of the test sample containing the test substance is denoted as upstream or downstream, and the direction is defined as upstream or downstream.

DESCRIPTION OF THE PREFERRED EMBODIMENTS

Figure 1:
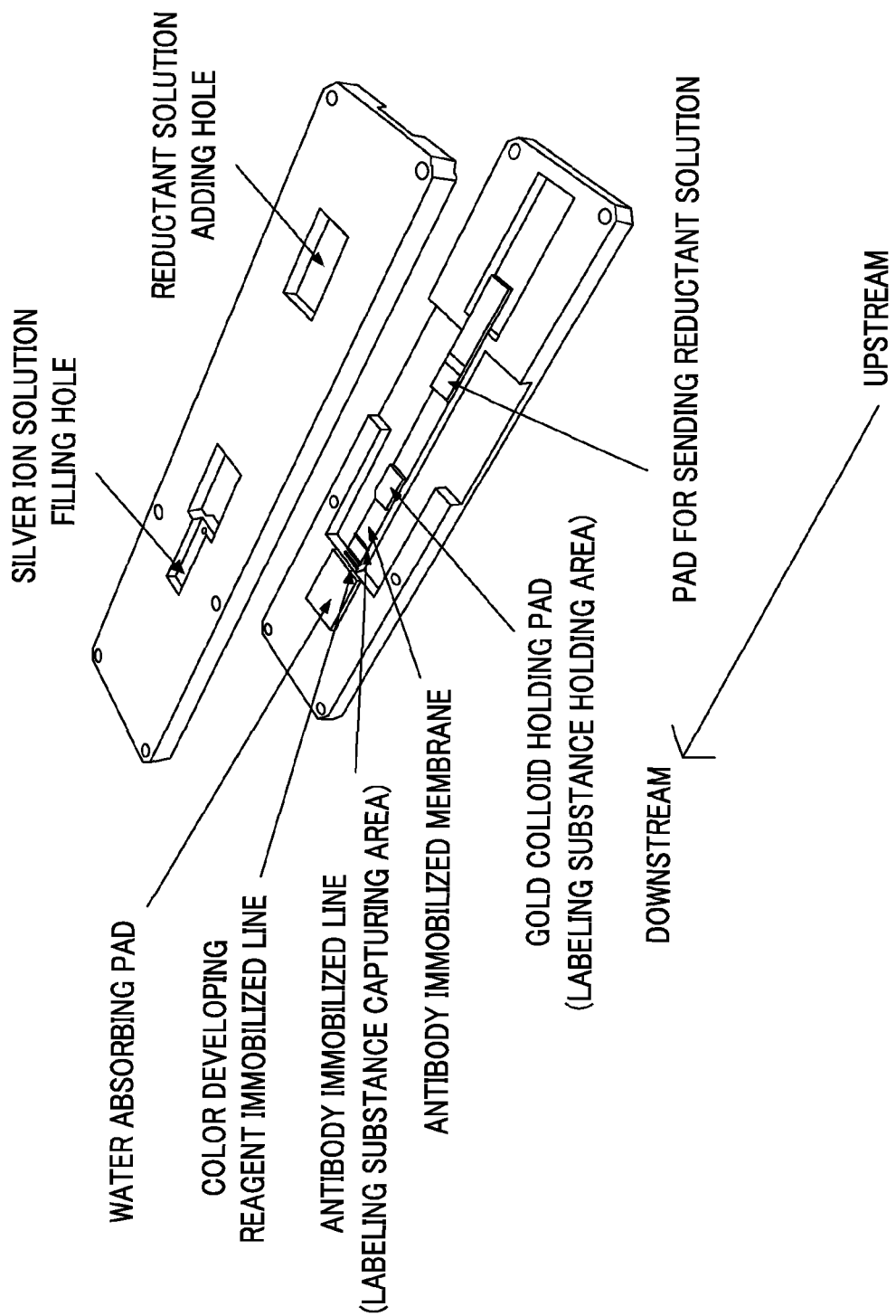
FIG. 1 shows an embodiment of a kit used in Examples. In the second member of the upper portion constituting the external portion of the kit of the present invention, a silver ion filling hole which is a second amplification reagent and a reductant solution adding hole which is a first amplification reagent are arranged. In the first member of the lower portion, a pad for flowing the reductant solution which is the first amplification reagent, a colloidal gold holding pad which is a labeling substance holding area, an antibody immobilized membrane having an antibody immobilized line which is a labeling substance capturing area and a color developing reagent immobilized line which is an area having a color developing reagent, and a water absorbing pad are arranged in this order on an adhesive sheet.

Hereinafter, the present invention will be described in more detail.

The method of the present invention is a chromatography method including:

a step of forming a composite with a test substance and a labeling substance containing a metal modified by a first binding substance of the test substance and then developing the composite on an insoluble carrier;

a step of capturing the test substance and the labeling substance in a detection site on the insoluble carrier including a second binding substance of the test substance or a substance having a binding property to the first binding substance of the test substance; and a step of amplifying the captured labeling substance using a first amplification reagent and a second amplification reagent to detect the test substance, in which the position on the insoluble carrier to which the first amplification reagent is added is further upstream in the development direction than the position on the insoluble carrier to which the test sample containing the test substance is added;

the first amplification reagent is added onto the insoluble carrier within 0 seconds to 1 minute and 30 seconds after the test sample is added onto the insoluble carrier;

the first amplification reagent and the test sample are developed in the same direction on the insoluble carrier; and the second amplification reagent is infiltrated into the insoluble carrier in the thickness direction of the insoluble carrier. By this, it is possible to provide a chromatography method and a chromatographic kit, with which normal amplification can be carried out, background signals can be inhibited, and the operation is simple and convenient, and thus, measurement can be carried out rapidly.

In the method of the present invention, in a first feature, the position for addition when the first amplification reagent is added onto the insoluble carrier is further upstream in the development direction than the position on the insoluble carrier to which the test sample containing the test substance is added, whereby the amplification reaction can be achieved. In the case where the position for addition when the first amplification reagent is added onto the insoluble carrier is the same position as the position on the insoluble carrier to which the test sample containing the test substance is added or further downstream than the position on the insoluble carrier, the amplification reaction may not be achieved in some cases. This addition position of the first amplification reagent is not particularly limited as long as it is further upstream in the development direction than the addition position of the test sample, it is not particularly limited, but it is preferably on the upstream side by about 1 cm to 10 cm from the addition position of the test sample, and it may be more preferably on the upstream side by about 1 cm to 5 cm.

In the present invention, in a second feature, the first amplification reagent is added to the insoluble carrier within 0 seconds to 1 minute and 30 seconds after the test sample is added onto the insoluble carrier, and the first amplification reagent and the test sample are developed in the same direction on the insoluble carrier, whereby surprisingly, the background signals can be inhibited and further measurement can be carried out in a short time. Here, the same direction on the insoluble carrier refers to a direction in which the test sample and the first amplification reagent are developed along the longitudinal direction of the insoluble carrier from the upstream side to the downstream side. In the present invention, preferably, by adding a first amplification solution onto the insoluble carrier within 0 seconds to 1 minute and 30 seconds after the test sample is added onto the insoluble carrier, it is possible to further inhibit the background signals, which is the effect of the present invention. In order to carry out the measurement rapidly, it is more preferable to add the first amplification reagent at 0 seconds after the test sample is added onto the insoluble carrier (that is, simultaneously).

Figure 2:
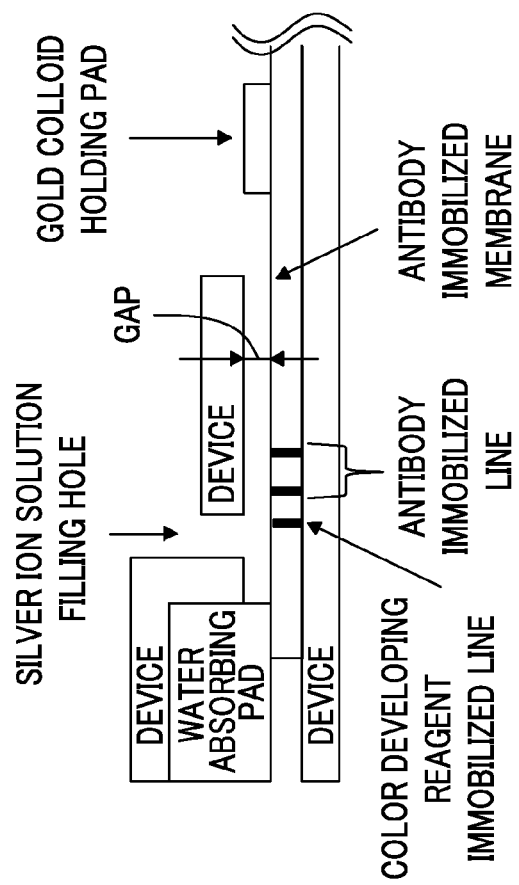
FIG. 2 shows a cross-sectional view in the horizontal direction on the downstream side of the kit used in Examples. A colloidal gold holding pad which is a labeling substance holding area and a water absorbing pad are arranged on an antibody immobilized membrane having an antibody immobilized line which is a labeling substance capturing area and a color developing reagent immobilized line which is an area having a color developing reagent. A device is arranged on the antibody immobilized membrane and a gap having a height of 0.15 mm is formed on the upper surface of the labeling substance capturing area.

Moreover, in the present invention, in a third feature, the second amplification reagent is infiltrated into the insoluble carrier in the thickness direction of the insoluble carrier (that is, perpendicular to the insoluble carrier), whereby it is possible to supply the second amplification solution uniformly. In FIG. 2 showing the immunochromatographic kit used in Examples of the present invention, a gap of about 0.15 mm is formed between the insoluble carrier and the device. Here, if a silver ion solution which is the second amplification reagent is added to a silver ion filling hole, the silver ion solution is supplied to the gap with a capillary force. Thereafter, the silver ion solution supplied to the gap is infiltrated into the insoluble carrier in the thickness direction of the insoluble carrier (antibody immobilized membrane) (that is, perpendicular to the insoluble carrier). The height of the gap between the insoluble carrier and the device is preferably about 0.01 mm to 1 mm. That is due to a fact that in the case where the height of the gap is less than 0.01 mm, it becomes difficult for the second amplification reagent to be supplied into the gap, whereas if the height of the gap is more than 1 mm, the capillary force is not exerted, and thus, it becomes difficult for the second amplification reagent to be uniformly added.

Since the chromatography method of the present invention has three features of the first to third features as described above, as the objects of the present invention, a normal and uniform amplification reaction can be achieved while the background signals are inhibited and unevenness in the amplification or the like is not generated, and further, measurement can be carried out simply and conveniently in a short measurement time.

1. Chromatography

The present invention aims to achieve the above-described objects in a chromatography method for amplifying detection signals. Generally, the chromatography method refers to a technique for determining and measuring a test substance simply, rapidly, and specifically by the following techniques. That is, a binding substance immobilized membrane (insoluble carrier) capable of having a labeling substance capturing area having at least one detection site having an immobilization reagent capable of binding to the test substance (corresponding to a second binding substance of the test substance, or a binding substance of the first binding substance below; specifically an antibody, an antigen, or the like) is used as a stationary phase. On this insoluble carrier, a solution including the labeling substance modified with the first binding substance of the test substance is used as a moving layer so as to move in the insoluble carrier chromatographically, and the moving layer reaches a labeling substance capturing area having the detection site while the test substance binds specifically to the labeling substance. In the detection site of the labeling substance capturing area, a composite of the test substance and the labeling substance specifically binds to the second binding substance or the binding substance of the first binding substance, which is immobilized, and thus, only in the case where a test substance is present in a test sample, the labeling substance is concentrated in the second binding substance or the binding substance of the first binding substance. The immunochromatography method is a technique that utilizes the above phenomenon and analyzes the presence of a test substance in a test sample qualitatively and quantitatively through visual observation or with an appropriate instrument.

In the chromatography method in the present invention, two types of amplification reagents are used to amplify the signal of the labeling substance, for example, preferably, a reductant for silver ions or a compound containing silver is used, and the signal is amplified by an amplification reaction using the composite of the test substance which binds to the immobilizing reagent on the labeling substance capturing area and the labeling substance being made to be a core, and as a result, high sensitivity may be achieved. According to the present invention, rapid highly-sensitivity chromatography can be carried out.

2. Test Sample

A test sample which can be analyzed using the chromatography method and the kit of the present invention is not particularly limited as long as the test sample is likely to include a test substance. Examples thereof include a biological sample, in particular, body fluids of animals (particularly a human) (for example, blood, serum, plasma, cerebrospinal fluid, lacrimal fluid, sweat, urine, pus, nasal discharge, and sputum) or an excretion (for example, excrement), organs, tissue, mucous membrane or skin, abraded specimens considered to contain these (swab), gargle liquid, or animals and plants themselves or dried bodies thereof. The test substance may include physiologically active substances such as natural substances, toxins, hormones, or pesticides, environmental pollutants, viruses, antigens, and antibodies.

3. Pre-Treatment of Test Sample

In the chromatographic method of the present invention, the test sample may be used as it is or in the form of an extract solution obtained from extracting the test sample using a suitable extracting solvent; in the form of a diluted solution obtained from diluting the extracted solution using a suitable diluting agent; or in a concentrated form of the extracted solution using a suitable method. As the extracting solvent used in the present invention, a solvent used in common immunological analysis (for example, water, a physiological sodium chloride solution, and a buffer solution), or a water-miscible organic solution in which the antigen-antibody reaction may be directly carried out by diluting the solution with such a solvent may also be used.

4. Configuration

In the chromatographic kit for carrying out the chromatography method of the present invention, a chromatographic strip may be installed and used. The chromatographic strip which may be used is not particularly limited as long as it is a chromatographic strip which can be used in common chromatography methods.

The chromatographic strip which may be used in the present invention has a labeling substance holding area and a labeling substance replenishing area from the upstream side to the downstream side of the development of a test sample including a test substance. In a preferable embodiment, the chromatographic strip further has an area having a color developing reagent. In a more preferable embodiment of the present invention, an embodiment in which an area having a color developing reagent is located downstream the labeling substance replenishing area is used, and furthermore, an embodiment in which a sample addition pad, a labeling substance holding pad having a labeling substance holding area (for example, a colloidal gold antibody holding pad), a binding substance immobilized membrane (for example, an antibody immobilized membrane having a labeling substance capturing area) which is an insoluble carrier, and a water absorbing pad are arranged in this order on an adhesive sheet is preferably used. The binding substance immobilized membrane which is an insoluble carrier has a labeling substance capturing area which is an area having at least one detection site in which an antibody or an antigen specifically bound to a test substance is immobilized, and may further have a control zone (also may be described as a control area in some cases), which is an area in which an antibody or an antigen for control is immobilized, if desired.

The labeling substance holding pad having a labeling substance holding area, which may be used in the present invention, may be prepared by preparing a suspension containing the labeling substance, coating the suspension on a suitable water absorbing pad (for example, a glass fiber pad), and then drying it.

4-1. Labeling Substance

As the labeling substance used in the present invention, a labeling substance containing a metal is used as a label used for labeling a first binding substance that specifically binds to a test substance (antigen). As a type of the metal which may be used in the present invention, preferably, noble metals such as gold, silver, and platinum, iron, lead, copper, cadmium, bismuth, antimony, tin, mercury, or the like may be used, and more preferably noble metals such as gold, silver, and platinum may be used. As a preferable form of the labeling substance containing a metal which may be used in the present invention, a colloidal metal label or a metal sulfide label may be used. In the present invention, as the colloidal metal label, preferably colloidal platinum, colloidal gold, colloidal silver, colloidal iron, colloidal aluminum hydroxide, or the like may be used, and as the metal sulfide label, preferably, each sulfide of iron, silver, lead, copper, cadmium, bismuth, antimony, tin, or mercury may be used. In the present invention, even more preferably, colloidal platinum, colloidal gold, or colloidal silver, and most preferably, colloidal gold may be used. In the case where colloidal gold particles are used as a colloidal metal label, commercially available products may be used. Alternatively, colloidal gold particles may be prepared in a usual manner, for example, a method in which chloroauric acid is reduced with sodium citrate (Nature Physical Science, 241 (1973) 20, and the like).

The average particle diameter of the colloidal metals is preferably from about 1 nm to 500 nm, more preferably from 3 nm to 100 nm, and particularly preferably from 5 nm to 60 nm. The average particle diameter of the colloidal metals used in the present invention may be measured using a commercially available particle size distribution analyzer, or the like. As methods of measuring particle size distribution, an optical microscopy method, a confocal laser microscopy method, an electron microscopy method, an atomic force microscopy method, a static light scattering method, a laser diffraction method, a dynamic light scattering method, a centrifugal sedimentation method, an electrical pulse measurement method, a chromatography method, an ultrasonic attenuation method, and the like, are known, and devices that support each principle are commercially available.

A dynamic light scattering method can be preferably used in the present invention in view of the particle range and eases of measurement. Examples of the commercially available measuring devices using dynamic light scattering include Nanotrack UPA (Nikkiso Co., Ltd.), a dynamic light scattering-type particle size distribution measuring device LB-550 (Horiba, Ltd.), and a concentrated system particle size analyzer FPAR-1000 (Otsuka Electronics Co., Ltd.), and in the present invention, the average particle diameter is determined as the value of a median diameter (d=50) measured at a measurement temperature of 25° C.

According to the present invention, signals of the metal-based label may be amplified in chromatography using a colloidal gold label or a metal sulfide label, other metal alloy labels (which may be hereinafter referred to as a metal-based label in some cases), and a polymer particle label including a metal as the labeling substance for detection. Specifically, if the silver ions supplied from a compound containing silver such as an inorganic silver salt and an organic silver salt is brought into contact with a reductant for silver ions and silver particles are produced by the reduction of the silver ions using the reductant after the composite of the test substance and the labeling substance for detection is formed, a highly sensitive analysis of the test substance may be carried out by the metal-based label being amplified since the silver particles are deposited on the metal-based label with the metal-based label being a core. Therefore, in the chromatography method of the present invention, well-known chromatography methods in the related art may be used as it is except for a fact that a reaction which uses silver particles generated from the action of silver ions being reduced using the reductant to deposit on the label of the immune composite is carried out and the signal amplified in this way is analyzed.

4-2. Binding Substance

In the present invention, the labeling substance is modified with the first binding substance of the test substance. As the first binding substance, for example, any of an antibody to the test substance (antigen), an antigen for the test substance (antibody), an aptamer of the test substance (protein, a low-molecular compound, or the like), and a compound having an affinity for the test substance may be used.

The chromatographic kit of the present invention has (a) the second binding substance of the test substance or (b) a binding substance having a binding property with respect to the first binding substance in the labeling substance capturing area. As the second binding substance of the test substance, for example, any one of an antibody to the test substance (antigen), an antigen for the test substance (antibody), an aptamer of the test substance (protein, a low-molecular compound, or the like), and a compound having an affinity for the test substance may be used. Further, the second binding substance may be different from or the same as the first binding substance. The binding substance of the first binding substance may be a test substance itself, and a compound having a site which the first binding substance recognizes, and examples thereof include a compound to which a derivative of the test substance and protein (for example, BSA) are bound.

It is preferable that the first binding substance be an antibody and/or the second binding substance be an antibody. It is more preferable that the first binding substance be an antibody, and the second binding substance be an antibody which binds to the first binding substance.

In the chromatography method of the present invention, the antibody which has specificity with respect to the test substance is not particularly limited, however, for example, an antiserum prepared from the serum of an animal immunized by the test substance, an immunoglobulin fraction purified from the antiserum, a monoclonal antibody obtained by cell fusion which uses spleen cells of an animal immunized by the test substance or fragments thereof [for example, $F(ab')_2$, Fab, Fab', or Fv] may be used. The preparation of these antibodies may be carried out in a usual manner.

In the present invention, for example, as the method for modifying the labeling substance using the first binding substance, for example, when a colloidal metal and a specific binding substance are bound to each other, a method which follows well-known methods in the related art as described below (for example, The Journal of Histochemistry and Cytochemistry, 30, 7 (1982) 691-696) may be used. As specific examples thereof, a colloidal metal and a specific binding substance (for example, an antibody) are mixed for 5 minutes or more at room temperature in an appropriate buffer solution. After the reaction, the precipitates obtained by centrifugation are dispersed into a solution including a dispersing agent such as polyethylene glycol, and a target colloidal metal labeled specific binding substance may be obtained.

4-3. Insoluble Carrier

As the insoluble carrier which may be used in the present invention, a porous carrier is preferable. In particular, a nitrocellulose membrane, a cellulose membrane, an acetyl cellulose membrane, a polysulfone membrane, a polyethersulfone membrane, a nylon membrane, glass fiber, non-woven fabrics, a cloth, or a thread is preferable.

In the present invention, it is preferable that the labeling substance capturing area of the insoluble carrier have a detection site, in which the second binding substance of the test substance or the binding substance of the first binding substance is immobilized. The second binding substance of the test substance or the binding substance of the first binding substance may be directly immobilized on parts of the insoluble carrier by physical or chemical binding, thereby forming a detection site, or may be physically or chemically bound to fine particles such as latex particles, these fine particles being trapped in parts of the insoluble carrier and immobilized, thereby forming a detection site. In addition, it is preferable that, the insoluble carrier be treated for non-specific adsorption prevention by a treatment using an inactive protein and the like, and used after the immobilization of the second binding substance or the binding substance of the first binding substance. For the insoluble carrier of the present invention, an embodiment involving plural binding sites may be preferably used, and further, as a part of the labeling substance capturing area, the control site as described above may be included, if desired.

4-4. Labeling Substance Holding Pad

In the present invention, it is a preferable embodiment that a labeling substance holding pad having a labeling substance holding area, which is preferably a colloidal gold holding pad in the present invention, be installed in the chromatographic kit and used. As the material of the labeling substance holding pad, for example, cellulose filter paper, glass fibers, non-woven cloth and the like may be preferably used, and a certain amount of the labeling substance prepared as described above is impregnated and dried, and this is made to be the labeling substance holding area.

4-5. Sample Addition Pad

In the chromatographic kit of the present invention, it is preferable that a sample addition pad be further installed and used. As the sample addition pad, an embodiment in which the sample addition pad not only accepts the sample containing the test substance added but also has a function to filter insoluble particles and the like in the sample is preferable. The material of a sample addition pad may include a material having uniform properties such as cellulose filter paper, glass fiber, polyurethane, polyacetate, cellulose acetate, nylon and cotton cloth. In addition, in order to prevent the non-specific adsorption of the test substance in the sample to the material of the sample addition pad and lowering of the degree of accuracy of the analysis at the time of the analysis, the material that the sample addition unit is composed of is sometimes treated for non-specific adsorption prevention in advance and used in the present invention. The sample addition pad may also serve as the labeling substance holding pad having a labeling substance holding area described in 4-4.

4-6. Water Absorbing Pad

In the present invention, a water absorbing pad may preferably be installed in the chromatographic kit and used. The water absorbing pad is a site which absorbs and removes the unreacted labeling substance and the like which does not become insoluble in the detecting unit of the chromatographic carrier and at the same time, physically absorbs the added sample by chromatographic development, and an absorbent material such as cellulose filter paper, non-woven cloth, a cloth, cellulose acetate or the like is used. The speed of the chromatography after a tip of the chromatographed added sample reaches the water absorbing pad depends on the material, size or the like of the water absorbing pad, therefore, the speed that matches the measurement of the test substance may be set by the selection.

5. Color Developing Reagent for Detecting First Amplification Reagent

In the chromatographic kit used in the present invention, the insoluble carrier preferably has an area having a color developing reagent for detecting the first amplification reagent out of two types of the amplification reagents used to amplify the signal of a labeling substance.

In the present invention, as a color developing reagent for detecting the first amplification reagent, for example, the use of a compound which develops color by reacting with ions is preferable. The first amplification reagent will be described later in the present specification, however, for example, a compound which develops color by reacting with $Fe^{2+}$ ions may be used as the color developing reagent when the first amplification reagent is a reagent including divalent iron ions ($Fe^{2-}$). As the compound which develops color by reacting with $Fe^{2+}$ ions, a compound which can develop color by forming a composite with $Fe^{2+}$ ions may be used. As specific examples of the compound which develops color by reacting with $Fe^{2+}$ ions, a compound having a phenanthroline skeleton [for example, 1,10-phenanthroline, 5-methylphenanthroline, 5-nitrophenanthroline, bathophenanthroline (4,7-diphenyl-1,10-phenanthroline), bathophenanthroline disulfonic acid, or the like], a compound having a bipyridine skeleton [for example, 2,2'-bipyridine, or the like], or the like, may be used, and a compound having a phenanthroline skeleton may be preferably used. Furthermore, a reagent which changes color shades due to a structural change caused by $H^+$ ions in order to detect the first amplification reagent may be preferably used if the pH of an aqueous solution including a test sample and an aqueous solution including the first amplification reagent is different. In particular, if the aqueous solution including the first amplification reagent is acidic (lower than pH 7 and the concentration of $H^-$ ions is high), it is preferable that a compound which develops color by reacting with $H^+$ ions which is a color developing reagent well known as a pH indicator for the acidic area (for example, a diazo-based color developing reagent such as methyl orange, methyl red, Congo red and methyl yellow, a sultone-based color developing reagent such as thymol blue, bromocresol green, bromocresol purple and bromothymol blue), or the like, be appropriately selected and used in accordance with the pH of an aqueous solution including the amplification reagent.

Among these, 1,10-phenanthroline, bathophenanthroline, or bromocresol green can be more preferably used.

Since it is preferable that the color reagent do not move on the insoluble carrier when an aqueous solution including the test sample or an aqueous solution including the first amplification reagent is developed, Log P (a partition coefficient in water and octanol) of the color developing reagent is preferably 4.0 or more, and more preferably 5.0 or more. As the Log P, an actual measured value may be used, however, a calculated value obtained from a chemical structure, or the like, may also be used as a simple method of determination. The method of calculating the Log P is preferably a calculation method used in ChemDrawPro version 12 by CambridgeSoft Corporation. The responsiveness of a typical color developing reagent and the Log P (according to a ChemDrawPro version 12) are shown in Table 1 below.

TABLE 1

| Compound Name | Responsiveness | LogP |
| --- | --- | --- |
| 2,2'-Bipyridine | $Fe^{2+}$ response | 1.88 |
| Bathophenanthroline disulfonic acid | $Fe^{2+}$ response | 0.52 |
| 1,10-Phenanthroline | $Fe^{2+}$ response | 2.2 |
| 5-Methylphenanthroline | $Fe^{2+}$ response | 2.69 |
| 5-Nitrophenanthroline | $Fe^{2+}$ response | 2.34 |
| Thymol Blue | pH response | 4.01 |
| Methyl Orange | pH response | 2.95 |
| Methyl Red | pH response | 3.63 |
| Congo Red | pH response | 3.63 |
| Methyl Yellow | pH response | 4.76 |
| Bathophenanthroline | $Fe^{2+}$ response | 5.55 |
| Bromocresol Green | pH response | 7.99 |
| Bromocresol Purple | pH response | 6.33 |
| Bromothymol Blue | pH response | 8.8 |

It is preferable that the area having a color developing reagent be located downstream of the labeling substance replenishing area having a detection site of the insoluble carrier. Examples of the method for holding the color developing reagent in the chromatographic kit include a method in which a water absorbing pad which will be described later is dipped in a color developing reagent solution, and dried under reduced pressure, and a method in which a color developing agent is coated in a line shape downstream a labeling substance replenishing area of an insoluble carrier, or the like.

If the color developing reagent substantially moves in the insoluble carrier when any of the aqueous solution including the test sample or the aqueous solution including the first amplification reagent is developed, it is preferable that the color developing reagent be included in the water absorbing pad, and used.

If the color developing reagent substantially does not move in the insoluble carrier when any of the aqueous solution including the test sample or the aqueous solution including the first amplification reagent is developed, it is preferable that the color developing reagent be carried on the insoluble carrier having a labeling substance capturing area.

An embodiment in which the color developing reagent is carried on the insoluble carrier is more preferable in the present invention in order to make it possible to display the first amplification reagent reaching the labeling substance replenishing area with a smaller time lag.

In the present invention, incorporation of the labeling substance holding area on the upstream side and of the labeling substance replenishing area on the downstream side in this order are defined as an upstream and a downstream with respect to the development direction of the test sample containing the test substance when the test sample is developed using capillary action or a water absorbing force in a case of using a water absorbing pad, and the like. In the specific embodiment of the present invention, as shown in FIG. 1, the labeling substance holding area is defined as an upstream and the labeling substance replenishing area as a downstream when the test sample and the like are developed from the labeling substance holding area toward the labeling substance replenishing area.

In a preferred embodiment of the present invention, the labeling substance capturing area being filled with the first amplification reagent is confirmed by developing the first amplification reagents of the two amplification reagents used to amplify the signal of the labeling substance captured in the labeling substance capturing area from the upstream side of the labeling substance capturing area to the downstream side of the labeling substance capturing area and detecting the physical or chemical changes in the area having a color developing reagent. As the physical or chemical changes in the area having a color reagent, color developments, fluorescence changes or the like, caused by the reaction between the first amplification reagent and the color developing reagent may be detected. It is preferable that the color development be detected. Such physical or chemical changes may be detected visually or detected using detection instruments.

6. Method of Immunity Test

Hereinafter, a sandwich-type method as specific embodiments according to the chromatography method of the present invention will be described.

In the sandwich method, while not particularly limited, for example, an analysis of the test substance may be carried out according to the following procedure. First, the first binding substance (for example, a first antibody) and the second binding substance (for example, a second antibody) having specificity with respect to a test substance (an antigen) are prepared in advance by the method described above. In addition, the labeling substance is modified in advance using the first binding substance. The second binding substance is immobilized on an appropriate insoluble carrier (for example, a nitrocellulose membrane, a glass fiber membrane, a nylon membrane, a cellulose membrane, or the like) and this is made to be a labeling substance capturing area, and the second binding substance is brought into contact with a test sample (or the extracted solution thereof) which has a possibility of including the test substance (an antigen), and binding with the second binding substance (an antigen-antibody reaction with a second antibody) occurs if the test substance is present in the test sample. When an excess of the labeling substance modified with the first binding substance is further brought into contact at the same time as or after the binding of the test substance and the second binding substance, a composite made of the immobilized second binding substance, the test substance (antigen) and the labeling substance modified with the first binding substance is formed if the test substance is present in the test sample.

In the sandwich method, after the reaction of the immobilized second binding substance with the test substance (an antigen) and the test substance with the first binding substance which modifies the labeling substance is completed, the labeling substance which did not form the immune composite is removed, and subsequently, for example, the labeling substance capturing area of the insoluble carrier is observed as it is, the labeling substance is detected or quantified, and the presence or absence or the amount of the test substance in the test sample may be measured. In the present invention, a signal from the labeling substance which forms such a composite is amplified and detected by supplying, for example, a reductant and a silver ion-containing compound.

7. Amplification Reagent

An amplification reagent is a solution in which chemicals included are catalytically reacted by an action of the labeling substance or the test substance, and therefore generates a colored compound, luminescence or the like and may cause an amplification of the signal. For example, on a metallic label, a silver ion solution which causes a precipitation of the metallic silver by a physical development or a solution of a phenylenediamine compound and a naphthol compound which becomes a dye due to an action of a peroxidase label and hydrogen peroxide may be included.

Specifically, a so-called developing solution as described in general books in the field of photochemistry (for example, "Basics of Photographic Science and Engineering—Silver Salt Photography—" (edited by The Society of Photography and Imaging of Japan, Corona Publishing Co., Ltd.), "Chemistry of Photography" (Akira Sasai, Photographic Industry Publication, Co., Ltd.), and "Latest Prescription Handbook" (Shinichi Kikuchi et al., Amico Publishing Company) may be used as an amplification solution having an amplification solution reagent, and a so-called physical developing solution which includes silver ions in the solution and is reduced with the colloidal metal or the like in which the silver ions in the solution becomes a core of the development as a center may be used as the amplification solution without being particularly limited.

In the present invention, two types of amplification reagents are used. It is preferable that, of the two types of the amplification reagents used to amplify the signal of the labeling substance captured in the labeling substance capturing area, the first amplification reagent be included in a first amplification solution and the second amplification reagent be included in a second amplification solution, and amplification be carried out by sequentially adding the first amplification solution and the second amplification solution. The first amplification solution is preferably added to a pad for sending the reductant solution, which is located upstream the labeling substance holding pad and the sample addition pad.

As specific examples of the amplification solution, a combination of the first amplification solution including a reductant for silver ions and the second amplification solution including a compound containing silver may be used.

Hereinafter, the reductant for silver ions included in the first amplification solution and the compound containing silver included in the second amplification solution, and the like, will be described.

7-1 Compound Containing Silver

As the compound containing silver, the compound containing silver ions, and an organic silver salt, an inorganic silver salt or a silver complex may be used. A compound containing silver ions with high-solubility in solvents such as water is preferable, and silver nitrate, silver acetate, silver lactate, silver butyrate, silver thiosulfate or the like may be included. Silver nitrate is particularly preferable. As the silver complex, a silver complex coordinated with a ligand having a water-soluble group such as a hydroxyl group or a sulfonic group is preferable, and silver hydroxy thioether or the like may be included.

It is preferable that the inorganic silver salt or the silver complex be included generally at 0.001 mol/m$^2$ to 0.2 mol/m$^2$, and preferably at 0.01 mol/m$^2$ to 0.05 mol/m$^2$ as silver.

7-2. Reductant for Silver Ions

The reductant for silver ions may be any inorganic or organic material or a mixture thereof as long as the silver ions are reduced to silver.

As the inorganic reductant, a reducing metal salt or a reducing metal complex salt capable of changing the valence of metal ions such as Fe$^{2+}$, V$^{2+}$, and Ti$^{3+}$ may be preferably included. When using the inorganic reductant, it is necessary that the ions oxidized are either removed or made to be harmless by complex formation or reduction. For example, in a system in which Fe$^{2+}$ is used as the reductant, Fe$^{2+}$ may be made to be harmless by forming a complex of Fe$^{3+}$ which has been oxidized, using citric acid or EDTA. In the present system, such an inorganic reductant is preferably used and a metal salt of Fe$^{2+}$ is more preferable.

Moreover, the main developing agent used in a wet silver halide photosensitive material (for example, methyl gallate, hydroquinone, substituted hydroquinone, 3-pyrazolidones, p-aminophenols, p-phenylenediamines, hindered phenols, amidoximes, azines, catechols, pyrogallols, ascorbic acid (or a derivative thereof), and leuco dyes) and other materials which are apparent for those skilled in the related art, for example, materials disclosed in U.S. Pat. No. 6,020,117 may be used.

As the reductant, an ascorbic acid reductant is also preferable. Useful ascorbic reductants include ascorbic acid and analogs, isomers, and derivatives thereof and, for example, D- or L-ascorbic acid and sugar derivatives thereof (for example, γ-lactoascorbic acid, glucoascorbic acid, fucoascorbic acid, glucoheptoascorbic acid, maltoascorbic acid), sodium ascorbate, potassium ascorbate, isoascorbic acid (or L-erythroascorbic acid), salts thereof (for example, alkali metal salts, ammonium salts, or salts known in the related art), enediol-type ascorbic acid, enaminol-type ascorbic acid, thioenol-type ascorbic acid or the like may be preferably included. In particular, D-, L-, or D,L-ascorbic acid (and alkali metal salts thereof) or isoascorbic acid (or alkali metal salts thereof) is preferable and a sodium salt is a preferable salt. A mixture of these reductants may be used, if necessary.

8. Other Auxiliaries

As other auxiliaries of the amplification solution, a buffering agent, a preservative, for example, an antioxidant or an organic stabilizer, or a rate adjusting agent may be included. As the buffering agent, for example, a buffering agent which uses acetic acid, citric acid, sodium hydroxide or a salt of any of these or tris(hydroxymethyl)aminomethane, or other buffering agents used in general chemical experiments may be used. These buffering agents are used appropriately and the pH may be adjusted to be optimized in the amplification solution. Further, an alkylamine as an antifogging agent may be used as an additive and dodecylamine is particularly preferable. Further, in order to enhance the solubility of these additives, a surfactant may be used and C$_9$H$_{19}$—C$_6$H$_4$—O—(CH$_2$CH$_2$O)$_{50}$H is particularly preferable.

As a method in which the amplification reagent is spotted on the chromatographic kit, a method in which the reductant solution as the first amplification solution is spotted on the pad for sending the reductant solution, and the silver ion solution as the second amplification solution is spotted in the labeling substance capturing area from the top is preferable.

The method in which the two types of the amplification reagents are included inside the chromatographic kit includes a method in which a pot including a solution containing each amplification reagent is disposed above the sites at which each amplification reagent is spotted. It is preferable that a pot including the silver ion solution (a second amplification solution) be provided above a silver ion filling hole and the reductant solution (a first amplification solution) be place above the pad for sending the reductant solution. From these arrangements, the solutions may flow by pressing each pot and may be spotted at predetermined sites.

9. Chromatographic Kit

The chromatography method of the present invention can be carried out using a chromatographic kit including a labeling substance containing a metal modified with a first binding substance of a test substance, and a second binding substance of the test substance, or an insoluble carrier including a substance having a first binding property with respect to the test substance. In this case, the chromatographic kit may have a labeling substance including a metal modified with the first binding substance of the test substance which is provided on the insoluble carrier in advance. Alternatively, the chromatographic kit may have the labeling substance including a metal modified with the first binding substance of the test substance which is provided separately from the insoluble carrier. In this case, measurement may be carried out using a method including, for example, mixing a labeling substance provided separately from an insoluble carrier with a test sample and then developing it on the insoluble carrier. Further, the immunochromatographic kit of the present invention may be provided with an amplification solution including a compound containing silver and a reductant for silver ions. As the examples and preferable ranges of the respective materials constituting the immunochromatographic kit, the examples and ranges described in the immunochromatography method or the like may be preferably used.

According to the present invention, there is provided a chromatographic kit including:

(1) a labeling substance containing a metal modified with the first binding substance of the test substance;

(2) a first member having an area to which a test sample containing the test substance is added and a labeling substance capturing area having a second binding substance of the test substance or the binding substance of the first binding substance in this order in the direction from upstream to downstream with respect to the development direction of the test sample containing the test substance; and (3) a second member having a hole positioned to add the first amplification reagent at a position further upstream in the development direction of the test sample than the area to which the test sample containing the test substance is added, and a hole positioned to add the second amplification reagent at a position further downstream in the development direction of the test sample than the labeling substance capturing area.

The labeling substance containing a metal modified with the first binding substance of the test substance may be arranged on the first member or may be provided separately from the first member.

By preferably arranging the first member and the second member in the chromatographic kit, a gap having a height of 0.01 mm to 1 mm is formed on the upper surface of the labeling substance capturing area. In addition, in order to further ensure the amplification reaction of the second amplification reagent being carried out, the first member preferably has an area having a color developing reagent for detecting the first amplification reagent.

The present invention will be described in more detail with reference to Examples below, but the present invention is not limited to Examples.

EXAMPLES (1) Preparation of Immunochromatographic Kit for Detection of Influenza Virus Antigen (1-1) Preparation of Colloidal Gold Modified with Anti-influenza Type A Monoclonal Antibody (Labeling Substance Modified with First Binding Substance of Test Substance)

1 mL of a 160 μg/mL anti-influenza type A monoclonal antibody (Anti-Influenza A SPTN-5 7307, Medix Biochemica) solution was added to a colloidal gold solution of which pH was adjusted by adding 1 mL of a 50 mM $KH_2PO_4$ buffer (pH 7.5) to 9 mL of a colloidal gold solution with a diameter of 50 nm (EM. GC50, BBI Corporation) and the mixture was stirred. After standing for 10 minutes, 550 μL of a 1% by mass aqueous solution of polyethylene glycol (PEG Mw. 20,000, Product No. 168-11285, manufactured by Wako Pure Chemical Industries, Ltd.) was added and the mixture was stirred, and subsequently 1.1 mL of a 10% by mass aqueous solution of bovine serum albumin (BSA FractionV, Product No. A-7906, manufactured by SIGMA) was added and the mixture was stirred. After this solution was centrifuged (Himac CF16RX, manufactured by Hitachi, Ltd.) for 30 minutes under the condition of 8,000×g and 4° C., the supernatant was removed leaving approximately 1 mL, and the colloidal gold was re-dispersed using an ultrasonic cleaner. After that, the resultant was dispersed to 20 mL of a colloidal gold preservative solution (20 mM Tris-HCl buffer (pH 8.2), 0.05% by mass polyethylene glycol (PEG Mw. 20000), 150 mM NaCl, 1% by mass BSA), was centrifuged again for 30 minutes under the condition of 8,000×g and 4° C., the supernatant was removed leaving approximately 1 mL, and the colloidal gold was re-dispersed using an ultrasonic cleaner, and the solution of the colloidal gold modified with antibody (50 nm) was obtained.

(1-2) Preparation of Colloidal Gold Holding Pad (Labeling Substance Holding Area)

Colloidal gold modified with an anti-influenza type A monoclonal antibody prepared in (1-1) was diluted by a colloidal gold coating solution (20 mM Tris-HCl buffer (pH 8.2), 0.05% by mass polyethylene glycol (PEG; molecular weight 20000), 5% by mass sucrose), and water, and diluted so that the optical density (OD) at 520 nm became 0.1. This solution was uniformly coated on a glass fiber pad (Glass Fiber Conjugate Pad, Millipore Corporation) which was cut to 8 mm×150 mm with 0.8 mL per each pad, and after being dried under reduced pressure for 12 hours and cut to 5 mm, the colloidal gold holding pad modified with an anti-influenza type A monoclonal antibody was obtained. The portion which holds the colloidal gold antibody corresponds to the labeling substance holding area.

(1-3) Preparation of Antibody Immobilized Membrane (Binding Substance Immobilized Membrane)

An antibody immobilized membrane 3 was made by immobilizing the antibody and the color developing reagent according to the following method with respect to the nitrocellulose membrane which was cut to 60 mm×300 mm (using a plastic backing, HiFlow Plus RF120, manufactured by Millipore Corporation). The long side of the membrane was set downward, and at the position of 15 mm from the bottom, the solution of anti-influenza type A monoclonal antibody (Anti-Influenza A SPTN-5 7307, manufactured by Medix Biochemica) prepared to be 1.5 mg/mL was coated in a line shape and was used as a detection site. In addition, at the position of 11 mm from the bottom, a solution of anti-mouse IgG antibody (anti-mouse IgG (H+L), rabbit F(ab')$_2$, Product No. 566-70621, manufactured by Wako Pure Chemical Industries, Ltd.) prepared to be 0.2 mg/mL was coated in a line shape and used as a control site. In the present invention, the detection site and the control site were matched to give an antibody immobilized line. Further, Bromocresol Green (manufactured by Wako Pure Chemical Industries, Ltd.) adjusted to be 30 mM was coated in a line shape and was made to be the color developing reagent immobilized line. The coated membrane was dried for 30 minutes at 50° C. using a warm air dryer. 500 mL of a blocking solution (50 mM boric acid buffer (pH 8.5) containing 0.5% by mass casein (derived from milk, Product No. 030-01505, manufactured by Wako Pure Chemical Industries, Ltd.)) was placed in a vat and was allowed to stand for 30 minutes as is. After that, the membrane was transferred and immersed in 500 mL of a cleaning and stabilizing solution (50 mM Tris-HCl (pH 7.5) buffer including 0.5% by mass sucrose and 0.05% by mass sodium cholate) placed in a similar vat and was allowed to stand for 30 minutes as is. The membrane was taken out from the solution, dried for 12 hours at room temperature, and cut to a width of 5 mm, thereby affording an antibody immobilized membrane. The detection site in which the anti-influenza type A monoclonal antibody is immobilized corresponds to the labeling substance capturing area, and the control site in which the anti-mouse IgG antibody is immobilized corresponds to a positive control area.

(1-4) Preparation of Silver Amplification Solution (1-4-1) Preparation of Reductant Solution 23.6 ml of a 1 mol/l aqueous solution of iron nitrate prepared by dissolving iron (III) nitrate nonahydrate (manufactured by Wako Pure Chemical Industries, Ltd., Product No. 095-00995) in water and 13.1 g of citric acid (manufactured by Wako Pure Chemical Industries, Ltd., Product No. 038-06925) were dissolved in 290 g of water. When these were all dissolved, 36 ml of nitric acid (10% by mass) was added and stirred using a stirrer, and 60.8 g of iron (II) ammonium sulfate hexahydrate (manufactured by Wako Pure Chemical Industries, Ltd., Product No. 091-00855) was added thereto, thereby affording a reductant solution.

(1-4-2) Preparation of Silver Ion Solution 8 ml of a silver nitrate solution (including 10 g of silver nitrate) and 24 ml of a 1 mol/l aqueous solution of iron nitrate were added to 66 g of water. Further, this solution and a solution in which 5.9 ml of nitric acid (10% by mass), 0.1 g of dodecylamine (manufactured by Wako Pure Chemical Industries, Ltd., Product No. 123-00246), and 0.1 g of a surfactant $C_{12}H_{25}$—$C_6H_4$—O—$(CH_2CH_2O)_{50}H$ were dissolved in advance in 47.6 g of water were mixed, thereby affording a silver ion solution.

(1-5) Preparation of Kit-1 for Assay

A schematic diagram of the kit components for assay is shown in FIG. 1. The materials for the first member of the upper portion and the second member of the lower portion, each of which constitutes the outside of the kit, were prepared by injection molding using polypropylene, and is hereinafter referred to as a device. The antibody immobilized membrane (the anti-influenza type A antibody and the anti-mouse IgG antibody immobilized membrane) prepared in (1-3) as shown in FIG. 1, the water absorbing pad (GB-140, manufactured by ADVANTEC MFS, Inc., cut to 100 mm×150 mm), the pad for sending the reductant solution (Glass Fiber Conjugate Pad, manufactured by Millipore Corporation), and the colloidal gold holding pad modified with the anti-influenza type A monoclonal antibody prepared in (1-2) at the center as the colloidal gold holding pad were loaded as shown in FIG. 1, thereby preparing a kit for assay.

(2-1) Example 1

(2-1-1) Development of Test Sample Solution (Specimen Solution)

A simulated positive specimen (BD Flu Examen control A+B—(manufactured by Becton, Dickinson and Company)) was 128-fold diluted with an extract (1% by mass BSA-PBS containing 1% by mass BIGCHAP), and 30 µL of this test sample solution was spotted to the colloidal gold holding pad modified with the anti-influenza type A monoclonal antibody.

(2-1-2) Development of Reductant Solution

Figure 3:
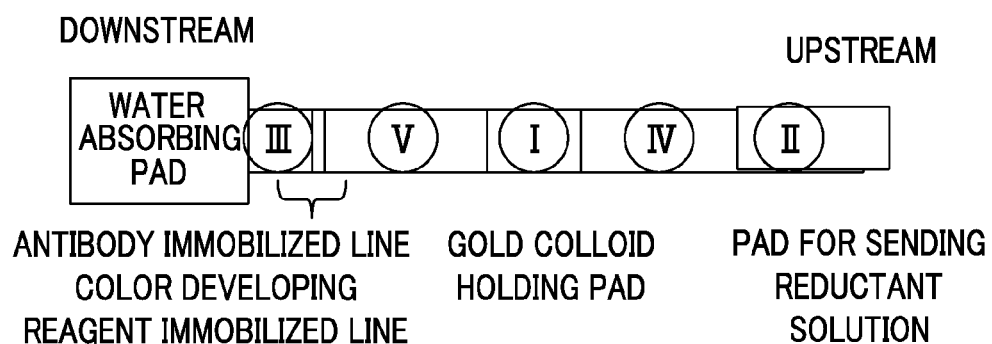
FIG. 3 shows positions to which the respective solutions are added in Examples and Comparative Examples. The position No. I shows a colloidal gold holding pad, the position No. II shows a pad (furthest upstream) for flowing the reductant solution, the position No. III shows a silver ion filling hole, the position No. IV shows a position between I and II, and the position No. V shows a position between I and the antibody immobilized line. The distance between the position Nos. I and II is 2 cm.

At the same time when the test sample solution was spotted in (2-1-1), the reductant solution was developed by spotting 200 µL of the reductant solution on the pad for sending the reductant solution (position II in FIG. 3). That is, the addition position of the reductant solution was further upstream the development direction than the addition position of the test sample solution, and the reductant solution and the test sample were developed in the same direction on the insoluble carrier.

(2-1-3) Silver Amplification

By adding 95 µL of the silver ion solution prepared in (1-5-2) to the silver ion solution filling hole in FIG. 1 after the color of the color developing reagent immobilized line changed from deep green to orange, the silver ion solution was infiltrated into the insoluble carrier in the thickness direction of the insoluble carrier to carry out silver amplification for 1 minute. Whether the antibody immobilized line could be detected or not was visually evaluated. The results were evaluated in three steps, "A", "B", and "C", as described later. Further, since the background density is quantitative, the silver-amplified membrane was taken out after visual evaluation and sufficiently washed with water for 3 minutes in order to prevent fogging due to light and imaged using a LAS 4000 (manufactured by Fujifilm Corporation) to measure the background density. The background density was expressed in an OD value of the site between the detection site and the control site of the antibody immobilized line.

(2-2) Example 2

(2-2-1) Development of Test Sample Solution (Specimen Solution)

A simulated positive specimen (BD Flu Examen control A+ B—(manufactured by Becton, Dickinson and Company)) was 128-fold diluted with an extract (1% by mass BSA-PBS containing 1% by mass BIGCHAP), and 30 µL of this test sample solution was spotted to the colloidal gold holding pad modified with the anti-influenza type A monoclonal antibody.

(2-2-2) Development of Reductant Solution

At the same time when the test sample solution was spotted in (2-2-1), the reductant solution was developed by spotting 200 µL of the reductant solution on the position IV in FIG. 3. That is, the addition position of the reductant solution was further upstream in the development direction than the addition position of the test sample solution, and the reductant solution and the test sample were developed in the same direction on the insoluble carrier.

(2-2-3) Silver Amplification

By adding 95 µL of the silver ion solution prepared in (1-5-2) to the silver ion solution filling hole in FIG. 1 after the color of the color developing reagent immobilized line changed from deep green to orange, the silver ion solution was infiltrated into the insoluble carrier in the thickness direction of the insoluble carrier to carry out silver amplification for 1 minute. Whether the antibody immobilized line could be detected or not was visually evaluated. The results were evaluated in three steps, "A", "B", and "C", as described later.

(2-3) Example 3

(2-3-1) Development of Test Sample Solution (Specimen Solution)

A simulated positive specimen (BD Flu Examen control A+B—(manufactured by Becton, Dickinson and Company)) was 128-fold diluted with an extract (1% by mass BSA-PBS containing 1% by mass BIGCHAP), and 30 µL of this test sample solution was spotted to the colloidal gold holding pad modified with the anti-influenza type A monoclonal antibody.

(2-3-2) Development of Reductant Solution

At 30 seconds after the test sample solution was spotted in (2-3-1), the reductant solution was developed by spotting 200 µL of the reductant solution on the pad for sending the reductant solution (position II in FIG. 3). That is, the addition position of the reductant solution was further upstream in the development direction than the addition position of the test sample solution, and the reductant solution and the test sample were developed in the same direction on the insoluble carrier.

(2-3-3) Silver Amplification

By adding 95 µL of the silver ion solution prepared in (1-5-2) to the silver ion solution filling hole in FIG. 1 after the color of the color developing reagent immobilized line changed from deep green to orange, the silver ion solution was infiltrated into the insoluble carrier in the thickness direction of the insoluble carrier to carry out silver amplification for 1 minute. Whether the antibody immobilized line could be detected or not was visually evaluated. The results were evaluated in three steps, "A", "B", and "C", as described later. Further, since the background density is quantitative, the silver-amplified membrane was taken out after visual evaluation and sufficiently washed with water for 3 minutes, and imaged using a LAS 4000 (manufactured by Fujifilm Corporation) to measure the background density. The background density was expressed in an OD value of the site between the detection site and the control site of the antibody immobilized line.

(2-4) Example 4

(2-4-1) Development of Test Sample Solution (Specimen Solution)

A simulated positive specimen (BD Flu Examen control A+B—(manufactured by Becton, Dickinson and Company)) was 128-fold diluted with an extract (1% by mass BSA-PBS containing 1% by mass BIGCHAP), and 30 µL of this test sample solution was spotted to the colloidal gold holding pad modified with the anti-influenza type A monoclonal antibody.

(2-4-2) Development of Reductant Solution

At 1.5 minutes after the test sample solution was spotted in (2-4-1), the reductant solution was developed by spotting 200 µL of the reductant solution on the pad for sending the reductant solution (position II in FIG. 3). That is, the addition position of the reductant solution was further upstream in the development direction than the addition position of the test sample solution, and the reductant solution and the test sample were developed in the same direction on the insoluble carrier.

(2-4-3) Silver Amplification

By adding 95 µL of the silver ion solution prepared in (1-5-2) to the silver ion solution filling hole in FIG. 1 after the color of the color developing reagent immobilized line changed from deep green to orange, the silver ion solution was infiltrated into the insoluble carrier in the thickness direction of the insoluble carrier to carry out silver amplification for 1 minute. Whether the antibody immobilized line could be detected or not was visually evaluated. The results were evaluated in three steps, "A", "B", and "C", as described later. Further, since the background density is quantitative, the silver-amplified membrane was taken out after visual evaluation and sufficiently washed with water for 3 minutes, and imaged using a LAS 4000 (manufactured by Fujifilm Corporation) to measure the background density. The background density was expressed in an OD value of the site between the detection site and the control site of the antibody immobilized line.

(2-5) Comparative Example 1

(2-5-1) Development of Test Sample Solution (Specimen Solution)

A simulated positive specimen (BD Flu Examen control A+ B—(manufactured by Becton, Dickinson and Company)) was 128-fold diluted with an extract (1% by mass BSA-PBS containing 1% by mass BIGCHAP), and 30 µL of this test sample solution was spotted to the colloidal gold holding pad modified with the anti-influenza type A monoclonal antibody.

(2-5-2) Development of Reductant Solution

At the same time when the test sample solution was spotted in (2-3-1), the reductant solution was developed by spotting 200 µL of the reductant solution on the position I in FIG. 3. That is, the addition position of the reductant solution was the same as the addition position of the test sample solution.

(2-5-3) Silver Amplification

By adding 95 µL of the silver ion solution prepared in (1-5-2) to the silver ion solution filling hole in FIG. 1 after the color of the color developing reagent immobilized line changed from deep green to orange, the silver ion solution was infiltrated into the insoluble carrier in the thickness direction of the insoluble carrier to carry out silver amplification for 1 minute. Whether the antibody immobilized line could be detected or not was visually evaluated. The results were evaluated in three steps, "A", "B", and "C", as described later.

(2-6) Comparative Example 2

(2-6-1) Development of Test Sample Solution (Specimen Solution)

A simulated positive specimen (BD Flu Examen control A+ B—(manufactured by Becton, Dickinson and Company)) was 128-fold diluted with an extract (1% by mass BSA-PBS containing 1% by mass BIGCHAP), and 30 µL of this test sample solution was spotted to the colloidal gold holding pad modified with the anti-influenza type A monoclonal antibody.

(2-6-2) Development of Reductant Solution

At the same time when the test sample solution was spotted in (2-6-1), the reductant solution was developed by spotting 200 µL of the reductant solution on the position Vin FIG. 3. That is, the addition position of the reductant solution was further downstream in the development direction than the addition position of the test sample solution.

(2-6-3) Silver Amplification

By adding 95 µL of the silver ion solution prepared in (1-5-2) to the silver ion solution filling hole in FIG. 1 after the color of the color developing reagent immobilized line changed from deep green to orange, the silver ion solution was infiltrated into the insoluble carrier in the thickness direction of the insoluble carrier to carry out silver amplification for 1 minute. Whether the antibody immobilized line could be detected or not was visually evaluated. The results were evaluated in three steps, "A", "B", and "C", as described later.

(2-7) Comparative Example 3

(2-7-1) Development of Test Sample Solution (Specimen Solution)

A simulated positive specimen (BD Flu Examen control A+ B—(manufactured by Becton, Dickinson and Company)) was 128-fold diluted with an extract (1% by mass BSA-PBS containing 1% by mass BIGCHAP), and 30 vEL of this test sample solution was spotted to the colloidal gold holding pad modified with the anti-influenza type A monoclonal antibody.

(2-7-2) Development of Reductant Solution

At 5 minutes after the test sample solution was spotted in (2-7-1), the reductant solution was developed by spotting 200 µL of the reductant solution on the pad for sending the reductant solution (position II in FIG. 3). That is, the addition position of the reductant solution was further upstream in the development direction than the addition position of the test sample solution, and the reductant solution and the test sample were developed in the same direction on the insoluble carrier.

(2-7-3) Silver Amplification

By adding 95 µL of the silver ion solution prepared in (1-5-2) to the silver ion solution filling hole in FIG. 1 after the color of the color developing reagent immobilized line changed from deep green to orange, the silver ion solution was infiltrated into the insoluble carrier in the thickness direction of the insoluble carrier to carry out silver amplification for 1 minute. Whether the antibody immobilized line could be detected or not was visually evaluated. The results were evaluated in three steps, "A", "B", and "C", as described later. Further, since the background density is quantitative, the silver-amplified membrane was taken out after visual evaluation and sufficiently washed with water for 3 minutes, and imaged using a LAS 4000 (manufactured by Fujifilm Corporation) to measure the background density. The background density was expressed in an OD value of the site between the detection site and the control site of the antibody immobilized line.

(2-8) Comparative Example 4

(2-8-1) Development of Test Sample Solution (Specimen Solution)

A simulated positive specimen (BD Flu Examen control A+ B—(manufactured by Becton, Dickinson and Company)) was 128-fold diluted with an extract (1% by mass BSA-PBS containing 1% by mass BIGCHAP), and 30 µL of this test sample solution was spotted to the colloidal gold holding pad modified with the anti-influenza type A monoclonal antibody.

(2-8-2) Development of Reductant Solution

At 30 minutes after the test sample solution was spotted in (2-8-1), the reductant solution was developed by spotting 200 µL of the reductant solution on the pad for sending the reductant solution (position II in FIG. 3). That is, the addition position of the reductant solution was further upstream in the development direction than the addition position of the test sample solution, and the reductant solution and the test sample were developed in the same direction on the insoluble carrier.

(2-8-3) Silver Amplification

By adding 95 µL of the silver ion solution prepared in (1-5-2) to the silver ion solution filling hole in FIG. 1 after the color of the color developing reagent immobilized line changed from deep green to orange, the silver ion solution was infiltrated into the insoluble carrier in the thickness direction of the insoluble carrier to carry out silver amplification for 1 minute. Whether the antibody immobilized line could be detected or not was visually evaluated. The results were evaluated in three steps, "A", "B", and "C", as described later. Further, since the background density is quantitative, the silver-amplified membrane was taken out after visual evaluation and sufficiently washed with water for 3 minutes, and imaged using a LAS 4000 (manufactured by Fujifilm Corporation) to measure the background density. The background density was expressed in an OD value of the site between the detection site and the control site of the antibody immobilized line.

(2-9) Comparative Example 5

(2-9-1) Development of Test Sample Solution (Specimen Solution)

A simulated positive specimen (BD Flu Examen control A+ B—(manufactured by Becton, Dickinson and Company)) was 128-fold diluted with an extract (1% by mass BSA-PBS containing 1% by mass BIGCHAP), and 30 µL of this test sample solution was spotted to the colloidal gold holding pad modified with the anti-influenza type A monoclonal antibody.

(2-9-2) Development of Reductant Solution

Figure 4:
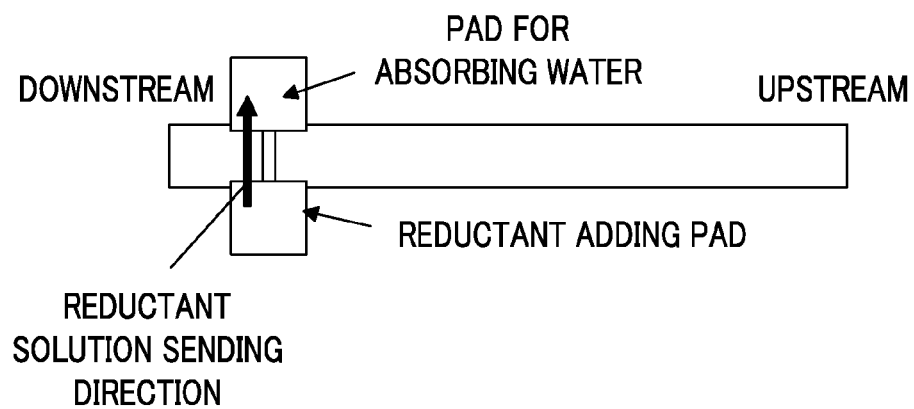
FIG. 4 shows a method for sending a reductant solution in Comparative Example 5. The direction for connecting a pad for adding a reductant with a pad for absorbing water (direction for sending a reductant solution) is arranged as perpendicular to the direction for flowing a test sample solution (specimen solution).

The test sample solution in (2-9-1) was spotted and allowed to stand for 10 minutes. The immunochromatographic strip was taken out of the device and all the pads were removed. A back adhesive sheet (ARcare 9020, NIPPN/TechnoCluster, Inc.) in 13 mm×8 mm attached to a pad for adding a reductant (glass fiber pad (Glass Fiber Conjugate Pad, Millipore Corporation) cut to 18 mm×8 mm) and a back adhesive sheet (ARcare 9020, NIPPN/Techno-Cluster, Inc.) in 13 mm×8 mm attached to a cellulose-glass membrane (CF6, Whatman plc) cut to 100 mm×8 mm) were attached, respectively, to the long side of the membranes. The position for membrane spotting was set such that the straight line connecting the pad for adding a reductant and the pad for absorbing water passed through the antibody immobilized line as in FIG. 4. Thereafter, the immunochromatographic strip was installed in the device again. It took 4 minutes for the operation of exchanging the pads. The pad for adding a reductant was leaned against the wall of a cubic container (length 9 mm×side 64 mm×height 25 mm) having 10 mL of the reductant solution inside to allow the pad for adding a reductant to be soaked in the solution, and the reductant solution was developed as it is for 10 minutes.

(2-9-3) Silver Amplification

By adding 95 µL of the silver ion solution prepared in (1-5-2) to the silver ion solution filling hole in FIG. 1, the silver ion solution was infiltrated into the insoluble carrier in the thickness direction of the insoluble carrier to carry out silver amplification for 1 minute. Whether the antibody immobilized line could be detected or not was visually evaluated. The results were evaluated in three steps, "A", "B", and "C", as described later. Further, since the background density is quantitative, the silver-amplified membrane was taken out after visual evaluation and sufficiently washed with water for 3 minutes, and imaged using a LAS 4000 (manufactured by Fujifilm Corporation) to measure the background density. The background density was expressed in an OD value of the site between the detection site and the control site of the antibody immobilized line.

(3) Results

The results of Examples 1 and 2 and Comparative Examples 1 and 2 are described in Table 2. A case where a black antibody immobilized line showed two separate lines was estimated as "A", and a case where the line could not be detected or unevenness in the amplification occurred, and accordingly, the line could not be identified was estimated as "C". As clearly seen from Table 2, by adding the reductant solution to the upstream portion with respect to the specimen and developing the specimen in the same direction, normal amplification was considered to be a success. In the case where the reductant solution was added to I and II, normal silver amplification was not carried out, and the line was almost not detected.

The results of Examples 1, 3, and 4 and Comparative Examples 3 to 5 are described in Table 3. A case where the black antibody immobilized line showed two separate lines was estimated as "A", a case where two separate lines could be seen, but there was sometimes no line due to occurrence of unevenness in the amplification was estimated as "B", and a case where the line could not be detected or unevenness in the amplification occurred, and thus, the line could not be identified was estimated as "C". In Examples 1, 3, and 4 and Comparative Examples 3 and 4, the timing at which amplification could be carried out was taken as a time at which the color of the color developing reagent immobilized line changed from deep green to orange. In Comparative Example 5, a time at 10 minutes after the addition of the specimen solution was taken as a timing at which amplification could be carried out. The time taken from the addition of the specimen solution to the colloidal gold holding pad to the completion of the silver amplification was taken as a test time. As clearly seen from Table 3, it was found that normal amplification could be carried out by adding the reductant solution within 1.5 minutes after the addition of the specimen solution. In particular, by adding the reductant solution within 30 seconds after the addition of the specimen solution, the time at which amplification could be carried out was not delayed, and thus, the test time was short. If the timing for adding the reductant solution after the addition of the specimen solution was 5 minutes or more, an increase in the background could be seen, and if the timing was 30 minutes, unevenness in the amplification occurred, but surprisingly in the case where the reductant solution was added within 1.5 minutes after the addition of the specimen solution, the background density could be inhibited to be low. By increasing the timing for adding the reductant, by the effect of drying the membrane, the labeling substance is hardly washed out from this insoluble carrier, and thus, it is estimated that a failure in amplification and an increase in the background density occurred. Comparative Example 5 is an example in which the reductant solution (washing solution) was developed in the direction at 90 degrees with respect to the development of the specimen solution, but although the amplification was carried out normally, the test time was long due to the time for installation of the pad or the like, as compared with Examples 1, 3 and 4. As seen from Tables 2 and 3, the reductant solution is added further upstream than the addition position of the specimen solution, at the same time as the specimen solution or within 1 minute and 30 seconds after the addition of the specimen solution. Further, the reductant solution is developed in the same direction as that of the specimen solution, and the silver ion solution is infiltrated into the insoluble carrier in the thickness direction of the insoluble carrier. Thus, it is possible to perform normal amplification as well as to inhibit the background signals, and it is also succeeded to shorten the test time.

TABLE 2

| | Addition positions of three solutions | | | | |
|---|---|---|---|---|---|
| Test No. | Specimen (1st solution) | Reductant solution (2nd solution) | Silver ion solution (3rd solution) | Timing for adding reductant solution | Presence or absence of amplification |
| Example 1 | I | II | III | At the same time as addition of specimen | A |
| Example 2 | I | IV | III | At the same time as addition of specimen | A |
| Comparative Example 1 | I | I | III | At the same time as addition of specimen | C |
| Comparative Example 2 | I | V | III | At the same time as addition of specimen | C |

TABLE 3

| | Addition positions of three solutions | | | | Time taken from addition of reductant solution to amplification | Presence or absence of amplification | Measured value of background concentration | Test time |
|---|---|---|---|---|---|---|---|---|
| Test No. | Specimen (1st solution) | Reductant solution (2nd solution) | Silver ion solution (3rd solution) | Timing for adding reductant solution | | | | |
| Example 1 | I | II | III | At the same time as addition of specimen | 8 minutes | A | 0.103 | Short (9 minutes) |
| Example 3 | I | II | III | At 30 seconds after addition of specimen | 8 minutes | A | 0.103 | Short (9 minutes and 30 seconds) |
| Example 4 | I | II | III | At 1.5 minutes after addition of specimen | 9 minutes | A | 0.108 | Slightly long (11 minutes and 30 seconds) |
| Comparative Example 3 | I | II | III | At 5 minutes after addition of specimen | 9 minutes | B | 0.129 | Long (15 minutes) |
| Comparative Example 4 | I | II | III | At 30 minutes after addition of specimen | 9 minutes | C | 0.209 | Long (40 minutes) |
| Comparative Example 5 | I | Bat changed. Added to bat for addition of reductant solution | III | At 14 minutes after addition of specimen | 10 minutes | A | 0.103 | Long (25 minutes) |

What is claimed is:

1. A chromatography method comprising:
a step of developing a test substance and a labeling substance containing a metal, which is modified by a first binding substance against the test substance-in a composite state on an insoluble carrier;
a step of capturing a step of capturing the test substance and the labeling substance in a detection site on the insoluble carrier including a second binding substance of the test substance or a substance having a binding property to the first binding substance of the test substance; and
a step of amplifying the captured labeling substance using a first amplification reagent and a second amplification reagent to detect the test substance,
wherein the position on the insoluble carrier to which the first amplification reagent is added is further upstream in the development direction than the position on the insoluble carrier to which the test sample containing the test substance is added,
the first amplification reagent is added onto the insoluble carrier within 0 seconds to 30 seconds after the test sample containing the test substance is added onto the insoluble carrier;
the first amplification reagent and the test sample containing the test substance and the labeling substance are developed in the same direction on the insoluble carrier;
the second amplification reagent is infiltrated into the insoluble carrier in the thickness direction of the insoluble carrier,
the first amplification reagent is a reductant for silver ions and contains divalent iron ions and the second amplification reagent is a compound containing silver,
the insoluble carrier has an area having a color developing reagent for detecting the first amplification reagent, wherein the color developing reagent is a compound which develops color by reacting with ions and the area having a color developing reagent is located further downstream than the detection site on the insoluble carrier, and
the second amplification reagent is supplied to a gap having a height of 0.01 mm to 1 mm provided on the upper surface side of the insoluble carrier, and the second amplification reagent supplied to the gap is infiltrated into the insoluble carrier in the thickness direction of the insoluble carrier.

2. The chromatography method according to claim 1, wherein the development direction of the test sample and the first amplification reagent is the longitudinal direction of the insoluble carrier.

3. The chromatography method according to claim 1, wherein the color developing reagent is a compound which develops color by reacting with $Fe^{2+}$ ions.

4. The chromatography method according to claim 1, wherein the color developing reagent is a compound having a phenanthroline skeleton.

5. The chromatography method according to claim 1, wherein the color developing reagent is a compound which develops color by reacting with $H^+$ ions.

6. The chromatography method according to claim 1, wherein the first binding substance and/or the second binding substance is/are an antibody.

7. The chromatography method according to claim 1, wherein the labeling substance is a colloidal metal.

8. The chromatography method according to claim 1, wherein the colloidal metal is a colloidal gold.

* * * * *